United States Patent [19]
Lauermann et al.

[11] 3,932,684
[45] Jan. 13, 1976

[54] PHENOLIC AGENTS FOR DISINFECTING STALLS

[75] Inventors: Georg Lauermann, Metzkausen; Uwe Trabitzsch, Langenfeld, both of Germany

[73] Assignee: Henkel & Cie G.m.b.H., Dusseldorf, Germany

[22] Filed: Apr. 1, 1974

[21] Appl. No.: 456,894

[30] Foreign Application Priority Data
Apr. 6, 1973  Germany............................ 2317225

[52] U.S. Cl. ................. 424/346; 424/343; 424/347; 424/351
[51] Int. Cl.² ......................... A01N 9/26; A01N 9/30
[58] Field of Search ............. 424/347, 351; 426/346

[56] References Cited
OTHER PUBLICATIONS

Merck Index 18th Ed. p. 1023 (1968).
Chemical Abstracts 61:13780$h$ (1964).
Chemical Abstracts 67:41234$f$ (1967).
Chemical Abstracts 73:P7002$t$ (1970).
Chemical Abstracts 64:20017$c,d$ (1966).

*Primary Examiner*—Leonard Schenkman
*Attorney, Agent, or Firm*—Hammond & Littell

[57] ABSTRACT

An agent for disinfecting stalls based on phenol or phenol derivatives, having a disinfecting action, and a solvent which penetrates the membranes of the parasitic spores, wherein a combination of perchloroethylene and a monohydroxy alcohol having 2 to 4 carbon atoms is used as said solvent.

8 Claims, No Drawings

PHENOLIC AGENTS FOR DISINFECTING STALLS

THE PRIOR ART

The health of animals in agricultural environments suffers to a great extent from diseases in the various species of animals, particularly poultry, pigs and cattle, caused by infestation with coccidiae and mawworms. These parasites live in and off of the intestinal tract and harm the animals by absorbing nutriment and causing wounds in the animals by boring into the stomach wall or intestine wall. In the case of mass infestation these parasites cause debilitation, distress or death as a result of toxic effects. Moreover, the parasites excrete highly resistant spores (mawworm eggs, *Coccidiae oocystae*) which are excreted with the dung and contaminate the stall.

Farmers use special disinfectants to kill these excreted, resistant forms of eggs, thus effectively interrupting, by disinfection, the cycle of excretion and re-absorption from the dung.

Worm or coccidiae control is effected in the following manner:

a. feeding the animals with vermifuges or coccidicidal agents in order to kill the parasites in the intestinal tract; and
b. special disinfection against excreted worm eggs and coccidiae oocystae in the stall.

Special known disinfectants based on phenolic active ingredients and carbon disulfide are already being used for disinfecting stalls. Carbon disulfide is used to penetrate the very solid membranes of these eggs or oocystae and to introduce therein the phenolic active ingredients for killing the contents of the egg and oocystae. However, the use of carbon disulfide for such purposes is not without danger due to the high risk of explosion and toxicity. Agents containing chlorinated hydrocarbons have also been proposed. However, these agents have not been used in actual practice due to their lack of efficacy.

OBJECTS OF THE INVENTION

It is an object of the present invention to provide a liquid concentrate agent for disinfecting stalls which is based on phenol or phenol derivatives, having a disinfecting action, and a solvent which penetrates the membranes of the parasitic spores, wherein a combination of perchloroethylene and a monohydroxy alcohol having 2 to 4 carbon atoms is used as said solvent.

It is a further object of the present invention to provide a method for disinfecting livestock stalls by spraying said stalls with an aqueous solution of said above-described liquid concentrate agent.

These and further objects of the present invention will become apparent as the description thereof proceeds.

DESCRIPTION OF THE INVENTION

This invention relates to agents for disinfecting stalls.

The present invention provides an agent for disinfecting stalls which is based on phenol or phenol derivatives, having a disinfecting action, and a solvent which penetrates the membranes of the parasitic spores, wherein a combination of perchloroethylene and a monohydroxy alcohol having 2 to 4 carbon atoms is used as said solvent.

More particularly the present invention provides liquid concentrate agent for a disinfecting stalls comprising a member having a disinfecting action selected from the group consisting of phenol and derivative of phenol, and a solvent combination which penetrates the membranes of parasitic spores and eggs consisting essentially of perchloroethylene and an alkanol having 2 to 4 carbon atoms.

Also the present invention is directed to an improved method of disinfecting livestock stalls which comprises spraying a solution of a disinfectant into a stall for livestock, wherein the improvement consists essentially of utilizing a solution of the above liquid concentrate agent as said disinfectant.

The phenol or phenol derivatives used in the stall disinfectants according to the invention must have a satisfactory disinfecting action, such as a phenol coefficient in the excess of 2 and adequate solubility in the solvents used. Preferably, chlorinated phenol derivatives such as p-chloro-m-cresol are used, although other phenol derivatives, such as cresols, o-phenylphenol, pentachlorophenol, and hexachlorophene are suitable.

Suitable examples of monohydroxy alcohols having 2 to 4 carbon atoms are alkanols having 2 to 4 carbon atoms, such as ethanol, propanol, isopropanol, butanol, isobutanol, and tertiary butanol, although isopropanol is preferably used. The solvent combination comprises perchloroethylene and the monohydroxy alcohol in a weight ratio of perchloroethylene to the alcohol of 1:0.05 to 1:5. Particularly satisfactory effectiveness with respect to the parasitic spores and eggs is obtained when there is a certain excess of alcohol over the perchloroethylene. Preferably, a weight ratio of perchloroethylene to alcohol of from 1:1.3 to 1:1.7 is used.

The amount of solvent (perchloroethylene plus alkanol) employed with reference to the amount of phenol or phenol derivatives is on the order of a ratio of 0.5 to 9:1.

In order to improve the wetting effect and the penetrative ability of the disinfectant, it is preferrable to add an anionic, a non-ionic, or a cationic surface-active compound to the disinfectant. The alkali metal salts, for example the sodium or potassium salts, the ammonium salts, or the lower alkyl-and alkylol-ammonium salts of fatty alcohol sulfates having 8 to 20 carbon atoms, alkyl sulfonates, having 8 to 20 carbon atoms, alkylbenzene sulfonates having 8 to 20 carbon atoms in the alkyl, and sulfosuccinic acid esters of alkanols having 8 to 20 carbon atoms are particularly suitable as anionic surface-active compounds. Suitable non-ionic surface-active compounds are particularly the polyalkylene glycol ether adducts, such as the adducts of ethylene oxide and/or propylene oxide, to fatty alcohols having 8 to 20 carbon atoms, fatty acids having 8 to 20 carbon atoms, fatty acid amides having 8 to 20 carbon atoms, fatty acid lower alkanolamides having 8 to 20 carbon atoms in the fatty acid, fatty amines having 8 to 20 carbon atoms, or alkylphenols having 8 to 20 carbon atoms in the alkyl. Examples of suitable non-ionic surface-active compounds are the adducts of 4 to 40, preferably 5 to 20 mols of ethylene oxide and/or propylene oxide to saturated or unsaturated fatty alcohols having 8 to 18 carbon atoms or fatty alcohol mixtures having 8 to 18 carbon atoms, or to nonylphenol. Finally, cationic surface-active compounds may be used which are derived preferably from quaternary ammonium compounds such as dodecyltrimethyl ammonium chloride or hexadecylpyridinium sulfate. These substances themselves have a partially disinfecting action.

The disinfectant agents according to the invention constitute liquid concentrates which have the characteristics of clear solutions or emulsions according to the particular surface-active compound employed. Preferably, these agents contain approximately 10% to 40% by weight of a phenol derivative,
10% to 50% by weight of perchloroethylene,
2.5% to 50% by weight of isopropanol, and
0% to 40% preferably 5% to 40%, by weight of a surface active compound.

Advantageously, a certain amount of water is added to the concentrates in order to improve the homogeneity and storage properties, and to facilitate the solubility in water when producing the diluted spray solutions. The quantity of water should be approximately 30% to 200% by weight of the concentrate. This amount of water is readily absorbed by the concentrate because of the presence of surface-active compound so that clear solutions will generally result.

The concentrates serve to produce dilute spray solutions having a content of approximately 0.3% to 3% by weight of phenol derivatives. There concentrates are usually diluted with anywhere from 3 to 133 times preferably 20 to 30 times, the weight of water so as to produce a dilute solution with from 0.3% to 3% by weight of the phenol. These solutions are applied in the stables, animal boxes, etc., in a known manner by spraying or atomizing; and these solutions will reliably kill eggs or oocystae of parasitic pests. A particular advantage of the agents according to this invention is that the concentration of toxic or combustible fumes occurring during manufacture and spraying is insufficient to constitute a risk of explosion, or fire, or the poisoning of personnel or useful animals. The concentrations of perchloroethylene measured in the air in the stalls after the spraying operation are substantially below the admissible and physiologically compatible values (MAK values). In contrast to this, it was ascertained that the admissible MAK value can be exceeded several times over when spraying agents containing carbon disulfide.

The following examples are merely illustrative of the present invention without being deemed limitative in any manner thereof.

EXAMPLE 1

A highly effective stall disinfectant concentrate was prepared from the following composition:

10 parts by weight of p-chloro-m-cresol,
10 parts by weight of perchloroethylene,
10 parts by weight of an aqueous 50% solution of the surface-active compound sodium alkylbenzene sulfonate having 8 to 20 carbon atoms in the alkyl and
15 parts by weight of isopropanol.

In order to improve the homogeneity and solubility in water, 55 parts by weight of distilled water were added to this preparation. Thus, a clear, liquid product was obtained which could readily be diluted with water in a ratio of approximately 1:12 to form a spray solution.

The spray solution was used in a conventional manner in a pigsty contaminated with mawworm eggs. Subsequent inspection showed that the treatment had killed virtually all the parasite eggs.

It was also established that the admissible MAK value for perchloroethylene (100 ppm) was not reached or exceeded during the spraying operation with the spray solution of the invention.

EXAMPLE 2

A highly effective stall disinfectant concentrate was prepared from the following composition:

15 parts by weight of o-phenyl-phenol,
10 parts by weight of perchloroethylene,
10 parts by weight of an aqueous 50% solution of the surface-active compound sodium alkylbenzene sulfonate having 8 to 20 carbon atoms in the alkyl,
30 parts by weight of isopropanol, and
35 parts by weight of distilled water.

This liquid concentrate was diluted with water in a ratio of 1:12 and was tested on eggs of ascaridia galli by bringing the eggs into contact with this diluted solution of the aforesaid disinfectant. The disinfectant was subsequently washed away and the eggs were fed to cows. No mawworm infestation was found in the intestines of the animals when they were slaughtered 4 weeks later.

EXAMPLE 3

A highly effective disinfectant concentrate was prepared analogously to Example 2, and was then diluted with water in a 1:12 ratio as in Example 2. In this experiment, conducted in vitro, it was found that the disinfectant was able to dissolve the mawworm eggs with a longer reaction period on the egg deposit.

Although the present invention has been disclosed in connection with a few preferred embodiments thereof, variations and modifications may be resorted to by those skilled in the art without departing from the principles of the new invention. All of these variations and modifications are considered to be within the true spirit and scope of the present invention as disclosed in the foregoing description and defined by the appended claims.

We claim:

1. A liquid concentrate for killing parasitic spores and eggs in livestock stalls comprising from 10% to 40% by weight of a disinfectant selected from the group consisting of phenol, p-chloro-m-cresol, cresol, o-phenyl-phenol, pentachlorophenol and hexachlorophene and a solvent combination which penetrates the membranes of parasitic spores and eggs consisting essentially of perchloroethylene and a monohydroxy alcohol having 2 to 4 carbon atoms; said liquid concentrate containing from 10% to 50% by weight of said perchloroethylene, from 25% to 50% by weight of said alcohol; and in addition containing from 0% to 40% by weight of a surface-active compound.

2. The concentrate of claim 1, in which the alcohol is isopropanol.

3. The concentrate of claim 1, in which the weight ratio of perchloroethylene to alcohol is 1:1.3 to 1:1.7.

4. The concentrate of claim 1, in which said disinfectant is selected from the group consisting of p-chloro-m-cresol and o-phenylphenol.

5. The concentrate of claim 1 in which said surface-active compound is an anionic surface-active compound which is an alkali metal salt of an alkylbenzene sulfonate having 8 to 20 carbon atoms in the alkyl.

6. The concentrate of claim 1, further comprising from 30% to 200% by weight of water, based upon the weight of said concentrate.

7. A disinfectant solution for killing parasitic spores and eggs in livestock stalls comprising the liquid concentrate of claim 1 with from 3 to 133 times the weight of water, based upon the weight of said concentrate, with the proviso that the disinfectant solution contains from 0.3% to 3% by weight of said disinfectant.

8. A method of killing parasitic spores and eggs in livestock stalls comprising spraying into said stalls, an effective amount of an aqueous solution containing a liquid concentrate comprising 10% to 40% by weight of a disinfectant selected from the group consisting of phenol, p-chloro-m-cresol, cresol, o-phenyl-phenol, pentachlorophenol and hexachlorophene and a solvent combination which penetrates the membranes of parasitic spores and eggs consisting essentially of perchloroethylene and a monhydroxy alcohol having 2–4 carbon atoms; said liquid concentrate containing from 10% to 50% by weight of said perchloroethylene, from 2.5 to 50% by weight of said alcohol; and in addition containing from 0% to 40% by weight of a surface-active compound.

* * * * *